United States Patent [19]

Karcher et al.

[11] Patent Number: 4,804,358
[45] Date of Patent: Feb. 14, 1989

[54] CORONARY PERFUSION PUMP

[75] Inventors: Gilles Karcher, Nancy; Max Amor, Vandoeuvre; Roger Niddam, Le Rancy; Jean-Pierre Villemot, Nancy, all of France

[73] Assignee: Medicorp Research Laboratories Corporation, Boca Raton, Fla.

[21] Appl. No.: 831,352

[22] Filed: Feb. 20, 1986

[30] Foreign Application Priority Data

Feb. 20, 1985 [FR] France ................. 85 02429

[51] Int. Cl.⁴ ............................. A61M 1/03
[52] U.S. Cl. ....................... 600/17; 604/53; 604/118
[58] Field of Search ............. 128/1 D, 344; 604/53, 604/118, 96–103

[56] References Cited

U.S. PATENT DOCUMENTS

| 3,394,705 | 7/1968 | Abramson | 604/43 |
| 4,077,394 | 3/1978 | McCurdy | 128/1 D |
| 4,456,000 | 6/1984 | Schjeldahl et al. | 128/1 D |
| 4,459,977 | 7/1984 | Pizon et al. | 128/1 D |
| 4,493,697 | 1/1985 | Krause et al. | 128/1 D X |
| 4,531,936 | 7/1985 | Gordon | 128/1 D |
| 4,569,332 | 2/1986 | Schiff et al. | 128/1 D |
| 4,648,384 | 3/1987 | Schmukler | 128/1 D |

FOREIGN PATENT DOCUMENTS 2361123 10/1978 France.
2502499 10/1982 France.

Primary Examiner—Dalton L. Trulock

[57] ABSTRACT

Coronary perfusion apparatus in which a catheter is held in place in the coronary artery by an intra-aortic balloon. The catheter carries a pressure sensor which is positioned adjacent the heart valves. The pump supplies oxygenation blood to the catheter at a predetermined time in the cardiac cycle which exists downstream of the occlusion through openings in the catheter under the control of a synchronizing means which determines the time of perfusion in response to cardiac signals and to signals corresponding to the measurement mode by the pressure sensor.

11 Claims, 1 Drawing Sheet

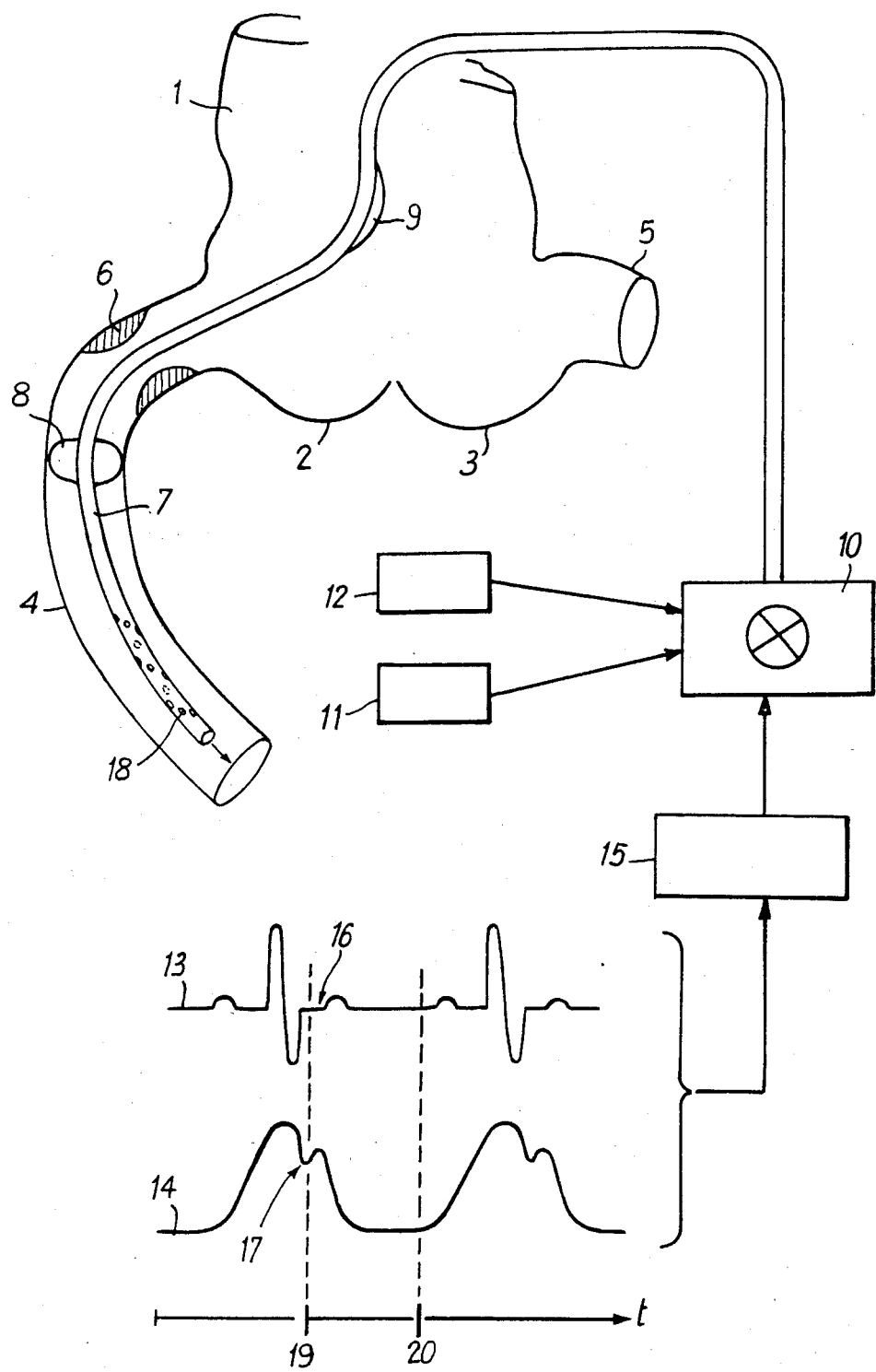

CORONARY PERFUSION PUMP

BACKGROUND OF THE INVENTION

The invention relates to a coronary perfusion pump that can bring therapeutic assistance in cases of insufficiency of coronary circulation.

This insufficiency is a situation frequently encountered, which is now treated medically or surgically. These treatments require a therapeutic supplement for several hours or several days, after which the patient can regain autonomy of the blood circulation.

The problem raised by the constriction of a coronary artery is not easy to solve. As a matter of fact, downstream of the constriction we note the appearance of an ischemic state due to a reaction of protection of the cells. To reestablish the circulation of the blood, the constriction can be eliminated by surgical intervention such as dilatation of the artery by an inflatable balloon, for example. But if the blood circulation is restored abruptly, it is found that cells which were insufficiently irrigated will die because they are suddenly over irrigated.

It is necessary to proceed with a gradual irrigation to insure the success of the intervention. It is therefore necessary to control the blood irrigation as a function of various parameters such as, in particular, the quantity, the temperature, the frequency, the quality of oxygenation of the blood and the presence of drugs.

One of the aims of the invention is to propse an assistance pump making it possible to bring into the coronary circulation oxygenated blood, which can contain drugs.

Another aim of the invention is to insure this assistance under optimal conditions of efficiency and without causing additional trauma.

BRIEF DESCRIPTION OF THE INVENTION

The subject of the present invention is a coronary perfusion pump for temporary therapeutic assistance in case of insufficiency of the coronary circulation. The pump includes a catheter having an end fixed in the coronary artery by means of an inflatable balloon. A pressure sensor is placed in the aorta opposite the cardiac valve; and there is a pump that can inject into the coronary artery, through the catheter, oxygenated blood and perhaps drugs.

According to other characteristics of the invention, the pump is placed under the control of a synchronizer that permits the injection of blood esentially during the diastolic period of the cardiac cycle. The synchronizer receives signals from an electrocardiogram and the pressure sensor and sends the pump the authorization to inject the blood only when these signals, corresponding to a definite point in the cardia cycle, coincide. In a preferred embodiment of the invention, the pressure sensor is carried by the catheter. The pump receives the blood to be injected from an oxygenator and the pump also can receive the drugs to be injected with the blood, the end of the catheter downstream of the inflatable balloon has a series of lateral perforations disposed in a spiral, in order to avoid problems of hemolysis.

BRIEF DESCRIPTION OF THE DRAWINGS

Other characteristics will appear on reading the description which follows, made in reference to the attached drawing which represents a schematic diagram of a coronary perfusion pump according to the invention.

DETAILED DESCRIPTION OF THE INVENTION

In the drawing, the cardiac mass is not represented. There is shown schematically the aorta 1, the corresponding cardiac valves 2, 3 and the coronary arteries, right 4 and left 5. In the example shown, coronary artery 4 has a constriction 6 which would often give rise to an insufficiency of coronary circulation. To provide circulatory assistance, the invention provides for the disposition of a catheter 7 equipped in the vicinity of its distal end with an inflatable balloon 8 which, on the one hand, insures the maintenance in position of the catheter 7 in the coronary artery 4, and on the other hand, the tight occlusion of the coronary artery 4 so as to exactly control the coronary perfusion downstream of the balloon.

The balloon 8 can be placed either downstream or upstream of the constriction 6. However, the end of the catheter 7 must extend beyond and downstream of the constriction. This end of catheter 7 is equipped with lateral perforations 18, preferably disposed in a spiral, to avoid the problems of hemolysis. The catheter 7 carries a pressure sensor 9 which must be situated in the aorta 1, opposite the cardiac valves 2, 3 to provide as well-defined a pressure reading as possible.

The catheter 7 is supplied by an assistance pump 10 capable of injecting definite quantities of oxygenated blood. This blood comes from the arteries of the patient himself or from a container, oxygenated by an outside oxygenator symbolized at 11. It can receive drugs, with a local effect, for example, in the form of a perfusate symbolized at 12.

The pump 10 is to inject the blood through the catheter 7 in a pulsed fashion during the diastolic phase of the cardiac cycle, that is to say when the arterial resistance is minimal. As a result, with an equal output, the pressure necessary to insure the coronary perfusion is minimal, reducing to a minimum the resulting trauma.

A precise definition of the instant of injection of the pump utilizes both the data from an electrocardiogram (ECG) and the pressures read by the pressure sensor 9, the graphs of which are shown respectively at 13 (ECG) and 14 (pressures). In practice the corresponding electrical signals are sent to a synchronizer 15 which gives pump 10 the authorization to inject blood only between the times 19 and 20 represented on the time scale t. This authorization is given only if the signals received by the synchronizer 15, corresponding to point 16 for the ECG and point 17 for the aortic pressure, coincide.

This precaution is necessary in order to be free of the frequency interference of ECG's and to allow for eventual disturbances in the cardiac rhythm. The synchronization of the signals from the ECG and the pressure sensor is indispensable for command of the coronary perfusion, on the one hand to avoid triggering an out-of-phase perfusion and on the other hand to facilitate monitoring by the attending personnel.

The assistance pump according to the invention therefore makes it possible to inject oxygenated blood and perhaps drugs into the coronary artery, for a period of several hours or several days. This system of assistance is, and should remain, temporary. This is why it is arranged to contribute as little trauma as possible in the management of the patient.

We claim:

1. A method for improvement of coronary blood circulation, comprising:
   inserting a sound into a coronary artery having an obstruction on an inside surface of a wall of said sound having an inflatable balloon at an end thereof and a plurality of lateral perforations positioned downstream of said inflatable balloon and going through the wall of the sound;
   fixing a position of the sound within the coronary artery by inflating said balloon in such a way that a portion of the sound having the perforations extends beyond said obstruction;
   injecting the blood through the sound by a pump in a pulsed fashion during a diastolic phase of the cardiac cycle when an arterial resistance is minimal;
   controlling the blood injection of the pump by means of a synchronizer utilizing signal from a pressure sensor situated within an aorta opposite cardiac valves and connected to said sound; and signals from an electrocardiogram;
   sending a signal by said synchonizer to the pump actuating injection of the blood only when the signals from the pressure sensor coincide with the signals from the electrocardiogram at the definite point of the cardiac cycle.

2. A method according to claim 1, wherein the pressure sensor is actuated by the sound.

3. A method according to claim 1 wherein the pump receives the blood for injection from an oxygenator.

4. A method according to claim 1 wherein the pump receives the drugs to be injected into the blood from a perfusate.

5. A method according to claim 1 wherein the lateral perforations are disposed in a spiral in order to avoid problems of hemolysis.

6. Coronary perfusion pump apparatus for improvement of coronary blood circulation comprising:
   a catheter adapted for insertion into a coronary artery having a plurality of perforations extending through the wall of said catheter near a downstream end thereof;
   inflatable balloon means coupled along said catheter upstream of said perforations for fixing said catheter within a coronary artery in the vicinity of a constriction by inflating said balloon;
   pumping means coupled to said catheter for injecting blood through said catheter in a pulsed fashion during a diastolic phase of a cardiac cycle when arterial resistance is at a minimum;
   a pressure sensor disposed along said catheter upstream of said balloon means;
   synchronizing means for controlling blood injection through said perforations in said catheter by said pumping means in accordance with pressure signals provided by said pressure sensor so as to inject blood into said artery at an ischemic zone downstream of said balloon means and at a predetermined time in the cardiac cycle.

7. Apparatus according to claim 6 and further comprising an electrocardiogram device for providing, in combination with said pressure sensor signals to said synchronizing means to inject blood during the diastolic phase of the cardiac cycle.

8. Apparatus according to claim 6 wherein said pressure sensor is attached to said catheter for placement in an aorta opposite the cardiac valves of a heart.

9. Apparatus according to claim 6 and further comprising an oxygenator coupled to said pumping means for supplying oxygenated blood.

10. Apparatus according to claim 6 and further comprising a perfusate coupled to said pumping means for injecting drugs into said blood.

11. Apparatus according to claim 6 wherein said perforations are disposed along a spiral on said catheter wall to reduce occurrence of hemolysis problems.

* * * * *